United States Patent [19]

Shalvi

[11] Patent Number: 5,251,637
[45] Date of Patent: Oct. 12, 1993

[54] ELECTRO-THERAPEUTIC DEVICE

[75] Inventor: Ram Shalvi, Kowloon, Hong Kong

[73] Assignee: Solar Wide Industrial Ltd., Hong Kong

[21] Appl. No.: 689,804

[22] PCT Filed: Nov. 2, 1989

[86] PCT No.: PCT/GB89/01309
§ 371 Date: May 21, 1991
§ 102(e) Date: May 21, 1991

[87] PCT Pub. No.: WO90/04997
PCT Pub. Date: May 17, 1990

[30] Foreign Application Priority Data

Nov. 2, 1988 [GB] United Kingdom ............. 8825604

[51] Int. Cl.$^5$ .................... A61H 39/02; A61N 1/36
[52] U.S. Cl. .................... 128/735; 128/907; 609/151
[58] Field of Search ........... 128/421, 731, 735, 800, 128/801, 907

[56] References Cited

U.S. PATENT DOCUMENTS

| | | | |
|---|---|---|---|
| 3,050,695 | 12/1962 | Du Vall | 128/421 |
| 3,894,532 | 7/1975 | Morey | 128/735 |
| 3,946,745 | 3/1976 | Hsiang-Lai et al. | 128/421 |
| 4,124,030 | 11/1978 | Roberts | 128/422 |
| 4,180,079 | 12/1979 | Wing | 128/422 |
| 4,408,617 | 10/1983 | Auguste | 128/735 |
| 4,541,432 | 9/1985 | Molina-Negro et al. | 128/421 |
| 4,694,840 | 9/1987 | Kairis et al. | 128/735 |
| 5,012,816 | 5/1991 | Lederer | 128/800 |

FOREIGN PATENT DOCUMENTS

| | | | |
|---|---|---|---|
| 0145176 | 6/1985 | European Pat. Off. | |
| 0850081 | 7/1981 | U.S.S.R. | 128/735 |
| 1194417 | 11/1985 | U.S.S.R. | 128/907 |
| 1416141 | 12/1975 | United Kingdom | |
| 2132893 | 7/1984 | United Kingdom | 128/801 |
| 9102559 | 7/1991 | World Int. Prop. O. | 128/735 |

Primary Examiner—Lee S. Cohen
Assistant Examiner—Jeffrey R. Jastrzab
Attorney, Agent, or Firm—Ostrolenk, Faber, Gerb & Soffen

[57] ABSTRACT

An electro-therapeutic device comprises an elongate hand held casing 1 having a tip electrode 4 at one end and an electrode 11 along one side. The tip electrode 4 is placed against the body and a high voltage (40 to 90V) is passed between the electrodes to stimulate the body at low resistance or acupuncture points. In a first aspect of the invention a low voltage DC current passes through the body and changes in the resistance of the body are used to modulate an audible signal to indicate when a low resistance point is reached. In a second aspect the casing 1 is of elongate cross-section so that electrode 11 sits snugly in the web of the hand. In a third aspect of the invention a pulsed, bipolar waveform is applied to the electrodes to avoid electrolytic action in the body. A solid state (transistor/diode) switch is also described for connecting the electrodes across a secondary winding of a transformer during a stimulation mode.

13 Claims, 3 Drawing Sheets

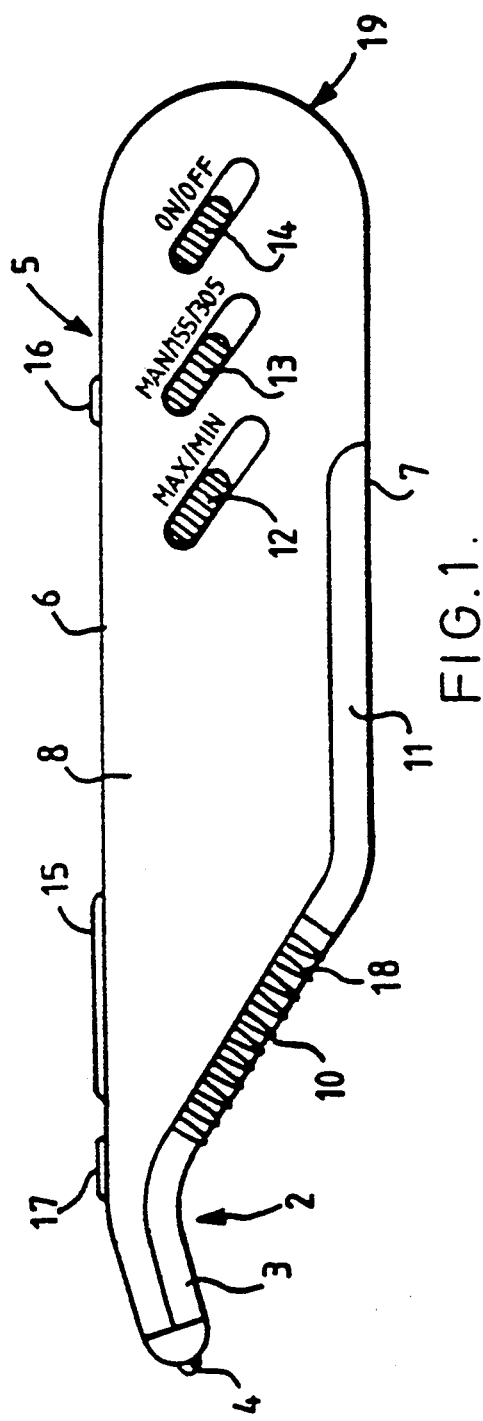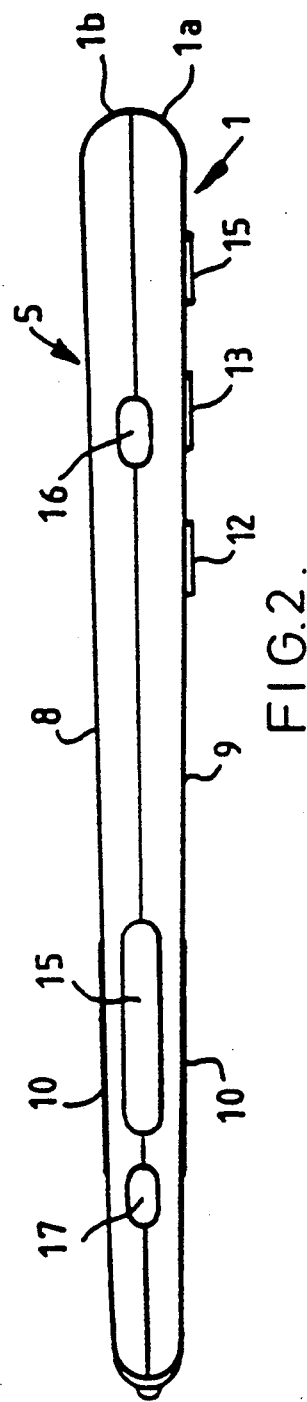

ELECTRO-THERAPEUTIC DEVICE

BACKGROUND OF THE INVENTION

The present invention relates to an electro-therapeutic device for applying a small electric current to the body. The application of small currents to particular points of the body, such as acupuncture points, biologically active trigger points, neural junctions etc., has been found to provide relief for certain ailments. Such points may be characterised by having a low electrical resistance compared to adjacent areas on the body.

GB1416141 describes a hand-held device in which a casing forms one electrode and is gripped in the hand. A second electrode projects from an end of the casing and is pressed against the body. A switch connects a 9V DC power supply across the electrodes. As the second electrode is passed over the surface of the body it encounters low resistance points so that a higher current flows through the body from the hand to the second electrode. Stimulation of the body at such low resistance points by the application of a low current which passes through the low resistance point can give a desirable therapeutic effect. The device of GB1416141 includes a light emitting diode whose brightness is intended to vary with the current flowing through the body, and hence provide a rough visual indication of when a low resistance point has been reached.

EP0145176 describes a hand-held device in which the two electrodes are mounted at the tip of a casing. A DC voltage is applied across the electrodes and a low resistance point on the body is detected by an increase in current between the electrodes. This is displayed visually by a row of light emitting diodes, and audibly by a speaker in the casing which sounds when a low resistance point is reached. The user then operates a switch to apply a higher, pulsed, DC current to stimulate the body at the low resistance point. Circuitry can be provided to apply the higher current automatically when the detected resistance falls below a predetermined value.

These prior art devices suffer from a number of drawbacks. The device of EP0145176 will not operate efficiently when the skin is moist, for example due to perspiration. In such conditions the moist skin forms a low resistance path which shunts the current between the electrodes, so that the device always measures a low resistance and any treatment current will not pass under the skin to the treatment points.

SUMMARY OF THE INVENTION

A first aspect of the invention provides a hand-held electro-therapeutic device comprising a casing which is holdable in the hand characterised by first and second electrodes for making electrical contact with the body of a user, voltage applying means for applying an alternating voltage across the electrodes to pass a current through the body of the user to apply a stimulus thereto, and resistance detecting means for detecting when a said electrode is located at or near a low resistance point on the body, said detecting means comprising means for detecting variations in the resistance between the electrodes and means providing an audible signal proportional to the resistance, wherein the casing is elongate and the first electrode is mounted at one end thereof, the casing having transverse to the elongate direction thereof, a cross-section having major and minor axes, the major axis being longer than the minor axis, the second electrode being mounted on a wall of the casing at one end of the major axis.

Preferably, the detecting means emits a sound which changes volume and/or pitch, the volume and/or pitch being proportional to the resistance. In this way the user is able to tell when a low resistance point is approached and it is not necessary to fix a predetermined threshold on the volume or change of resistance which will trigger the detecting means.

This is particularly advantageous, for example, when detecting low resistance points when the skin is moist since the moist skin itself lowers the apparent impedence.

Also the application of a DC current may result in the electro deposition of materials in the body which is undesirable and, furthermore, we have found that the voltage applied to the body must be fairly high to ensure that sufficient current is applied to the body whilst it must be limited to avoid any risk of burning the skin during prolonged use.

A second aspect of the invention provides a hand-held electro-therapeutic device, comprising an elongate casing arranged to be held in the hand characterised by having a first electrode at one end thereof, the casing having, transverse to the elongate direction thereof, a cross-section having major and minor axes, the major axis being longer than the minor axis, a second electrode on a wall of the casing at one end of the major axis, and means for applying an alternating voltage across the electrodes to pass a current therebetween through the body of a user of the device to apply a stimulus thereto.

The tips of the fingers have a high electrical resistance, whereas the web of the hand, the region between the thumb and forefinger, is a low resistance point of the human body. By shaping the casing so that, when held, one of the electrodes will contact the skin in this region the efficiency of operation of the device is improved whilst the user need simply hold the device in what will be a most comfortable fashion.

The major axis is preferably at least twice as long as the minor axis.

A pair of substantially flat, parallel sidewalls joined at upper and lower edges thereof by upper and lower walls may be provided. The lower wall may be arcuate.

The second electrode may be mounted on or form at least part of the lower wall and is arcuate.

On the upper wall a control for starting the application of a stimulating voltage across the electrodes may be provided.

A third aspect of the invention provides a hand-held electro-therapeutic device, comprising a casing arranged to be held in the hand, characterised by first and second electrodes mounted on the casing for contact with the skin, and voltage applying means in the casing for applying a voltage across the electrodes to pass a current therebetween through the body of a user, wherein the voltage applying means comprises means for applying an alternating voltage between the electrodes to apply a stimulus to the body of a user of the device.

The voltage may be a bipolar pulsed waveform. The waveform may have a frequency of about 16 $HZ_z$. The peak of the voltage may be adjustable between about 40 and about 90 volts and the stimulating voltage may have no overall DC component.

By alternating the pulses and maintaining the overall DC current at zero, the risk of electroysis or deposition of chemicals in the body can be reduced.

The pulse width may be about 130 microseconds. Preferably, the waveform of the pulses is substantially square. A battery power supply may be housed in the casing.

The alternating voltage may be provided by means of a transformer having a centre-tapped primary winding, a capacitor connected to the centre-tap and an oscillator which alternately grounds either end of the primary winding to discharge the capacitor therethrough.

The secondary winding of the transformer may be connected substantially directly to one of the electrodes and the other end is connected to the other electrode by a pair of back to back transistors each having a diode connected thereacross.

Timer means may be provided for applying the stimulating voltage for a predetermined period of time.

A fourth aspect of the invention provides a hand held electro-therapeutic device having a search mode and a stimulation mode, said device comprising a casing which is holdable in the hand, characterised by first and second electrodes for making electrical contact with the body of a user, voltage applying means for applying, in said stimulation mode, an alternating voltage across the electrodes to apply a stimulus to the body of the user, and resistance detecting means for detecting, in said search mode, when a said electrode is located at or near a low resistance point, said resistance detecting means applying a DC voltage across the electrodes, wherein in said search mode said electrodes are connected across a DC power supply and in said stimulation mode said first and second electrodes are connected to a common point by means of respective first and second transistors each transistor having a respective first or second diode connected there-across to allow current to flow between said electrodes in a first direction via the first transistor and second diode and in a second direction via the second transistor and first diode.

Other preferred features and advantages of the invention will be apparent from the following description and the accompanying claims.

BRIEF DESCRIPTION OF THE DRAWINGS

The invention will be further described, by way of example only, with reference to the accompanying drawings, in which:

FIG. 1 is a side view of an embodiment of an electro-therapeutic device according to the invention;

FIG. 2 is a plan view of the device of FIG. 1;

DETAILED DESCRIPTION

Figure 3:
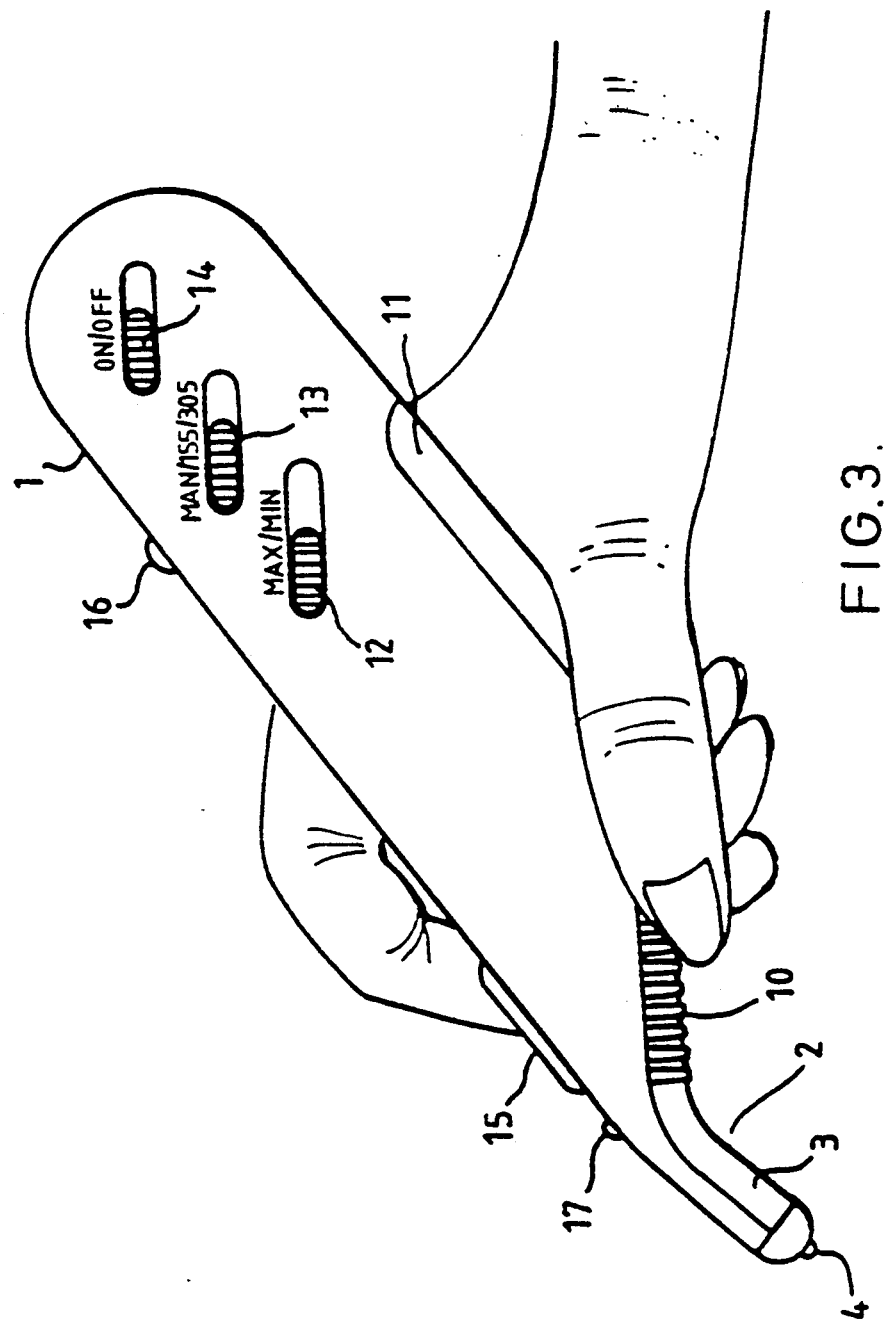
FIG. 3 shows the device of FIG. 1 held in the hand.

Referring to FIGS. 1 and 2, an electro-therapeutic device in accordance with the invention comprises a plastics casing 1 which is in two halves 1a, 1b. The casing 1 is elongate and ends at one end 2 in a nose 3 which carries a first, active, electrode 4 having a hemispherical tip of diameter about 3 mm. A body part 5 of the casing has upper and lower arcuate walls 6, 7 extending parallel to one another and flat, parallel side-walls 8, 9. The lower wall 7 curves up towards the upper wall 6 near the end 2, forming a ramp 10. A second, passive, electrode 11 extends along the lower wall 7 to present a large, exposed surface area. The side wall 9 carries control buttons 12, 13, 14 and the upper wall 6 carries a control button 15 and light emitting diode (LED) indicators 16, 17. An electrostatic speaker or buzzer B1 (see FIG. 4) is mounted in the casing behind the side wall 8.

The casing 1 houses circuitry (FIG. 4) for applying a voltage across the electrodes 4, ii. The casing may also house a power supply. In the example shown two 3V rechargeable cells are housed in the casing behind a removable cover 18 at the ramp 10. 6V DC power may be supplied from the mains via a separate transformer and fed to the circuit through a jack 19 in the other end of the casing 1. The circuit may also provide for recharging of the cells from the mains supplied input.

The device operates in one of two modes, a search mode for detecting a low resistance point on the body, which these typically correspond to nerve junctions or acupuncture points, and a stimulation mode for passing current through the body, between the electrodes 4, ii. The device is held in the hand (see FIG. 3) and is shaped so that the electrode 11 rests on the skin between the thumb and forefinger, which is a region of low resistance. The electrode 4 is then traced lightly over the skin.

In the search mode, a very low DC current, preferably up to a maximum of 3 microamps, is passed through the body between the points of contact of the electrodes 4 and 11 with the skin. The conductance of the body is thus measured and is converted to a variable frequency audio signal (speaker B1) which increases in pitch with increase in conductance. Hence, the low resistance points on the body can be detected by passing the electrode 4 across the skin and noting points at which the pitch of the sound from the speaker is highest.

In the stimulation mode, a higher amplitude, alternating, current is passed through the body between the electrodes to stimulate the body at a located low-resistance point.

The controls provided are an on-off switch 14, for switching the power to the circuitry on and off, a maximum/minimum slide switch 12 for controlling the intensity of the stimulation, a push-button type stimulation switch 15 for switching the device into the stimulation mode, and a three position timer switch 13 for controlling the stimulation period. The stimulation period may be set to, say, 15 seconds or 30 seconds, or to run continuously whilst the stimulation switch 15 is pressed. The on/off switch 14 and maximum/minimum switch 12 may incorporated into a single slide switch having an off position.

LED 17 flashes to indicate when the device is in the stimulation mode, whilst LED 16 flashes to indicate when the battery is low.

Figure 4:
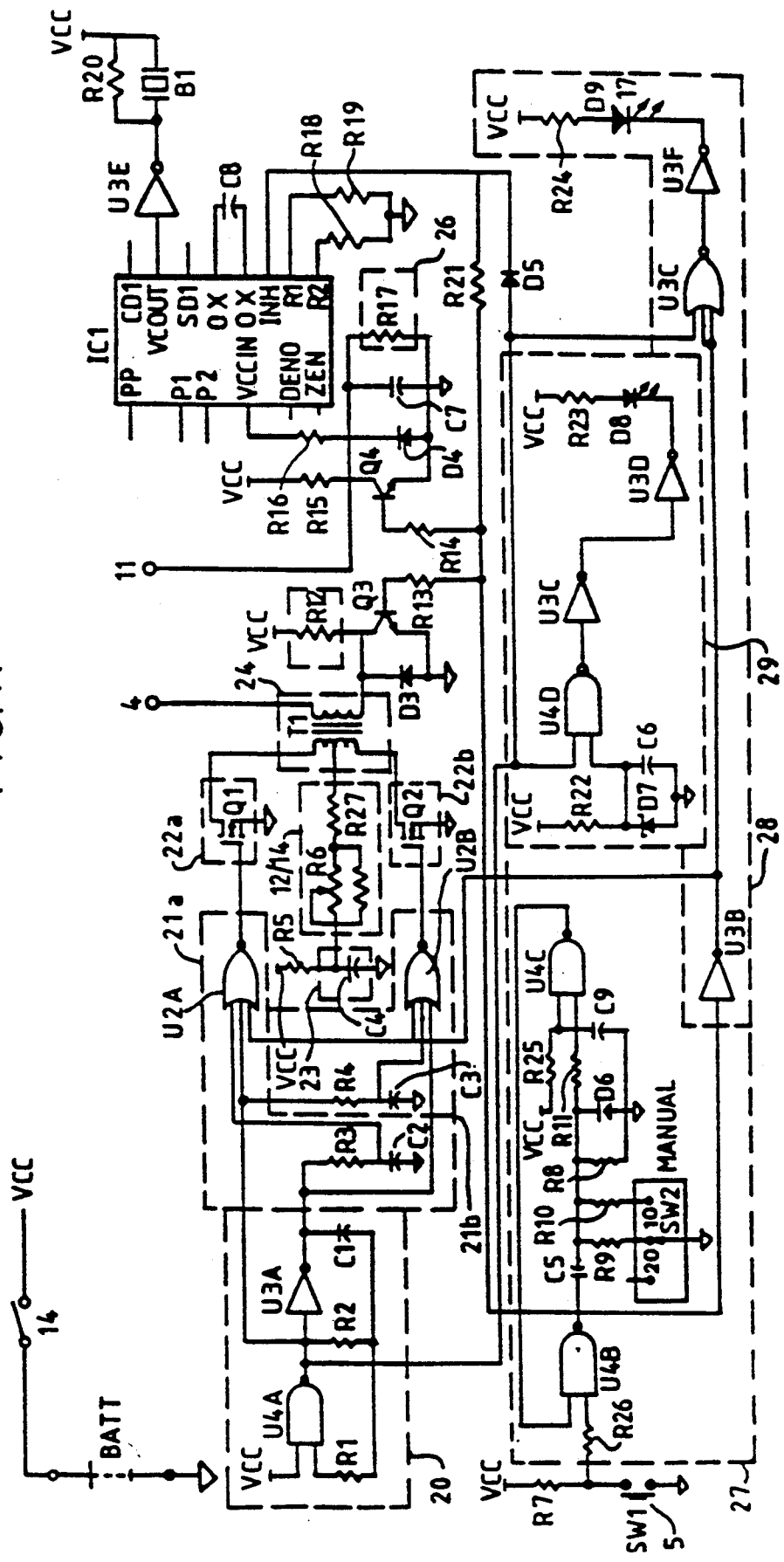
FIG. 4 is a circuit diagram of means for applying a voltage across the electrodes of the device of FIG. 1.

Referring to FIG. 4, the system is powered by two 3V rechargeable lithium cells (6V operating voltage). The circuit is driven by a 16 $HZ_z$ oscillator 20 (U4-A, U3-A, R1, R2, C1) which generates the stimulation signal, controls the flashing of the LED's and modulates the audio search signal.

Two transient detectors 21a, 21b are utilized to generate 130 microsecond pulses each time the oscillator changes state from low to high and high to low (R3, C2, U2-A and R4, C3, U2-B respectively). These pulses drive two FETS 22a, 22b (Q1, Q2) which discharge a capacitor 23 (C4) through an intensity control potentiometer (R6) (switch 12) and one branch of a centre tapped primary winding of a transformer 24 (T1). Capacitor 23 is connected to the centre-tap of the primary winding of the transformer 24, and is charged by the voltage supply Vcc through resistor R5. As an FET 22a or 22b is triggered by a pulse from a respective detector 21a, 21b, the capacitor 23 discharges to ground through the respective half of the primary winding via the respective FET which is connected between the outer end of the winding and ground. The capacitor 23 is charged via the resistor between the pulses. Resistor R5 limits the current flow from Vcc, while capacitor C5 discharges rapidly through the primary winding, the capacitance of C5 providing a limitation on the energy of the pulse induced in the secondary winding. Each time the capacitor discharges through the transformer, a high voltage low current pulse (maximum voltage about 90V, which will correspond to an instantaneous current of about 9 railliamps) is generated in the secondary winding of the transformer and serves as the stimulation signal. When the capacitor discharges via FET 22a (Q1), the secondary pulse is positive and when via FET 23b (Q2) it is negative. The intensity potentiometer controls the amount of current which flows during the capacitor discharge and therefore the output signal intensity. The potentiometer 12 includes a minimum resistance R27 to limit the maximum current flow, and hence intensity.

In the stimulation mode the transistors Q3, Q4 are turned on by the stimulation time control circuit 26 and, when necessary, switch 15. Thus electrode 11 is effectively connected to the opposite, lower end of the secondary winding of transformer T1 through a combination of transistor Q4 and diode D3 or transistor Q3 and diode D4 depending on the polarity of the secondary winding output. When the secondary winding output to electrode 4 is positive, current will flow through the body from electrode 4 to electrode 11 and the circuit is completed through transistor Q4 and diode D3. When the output to electrode 4 is negative, current flows through the body from electrode 11 to electrode 4, and the circuit from electrode 11 to the lower end of the secondary winding is completed through diode D4 and transistor Q3, via "ground".

A mode select control 27 is formed by a monostable (U4-B, U4-C, C5, R8, R9, R10, R11, D6, SW2) with three positions: 15 seconds, 30 seconds and manual. These are the preselected stimulation times available. In the manual position the unit will stimulate as long as the stimulation push-button switch 15 (SW1) is pressed. In all positions the stimulation will continue if the stimulation push button 15 is still pressed even if the selected time is over. A power up reset (R25, C9) is provided to ensure that when the unit is turned on it is in the search mode. R7 is the pull-up resistor to the stimulation switch. R26 is to protect the monostable input. A stimulation indicator 28 flashes an LED (17) in the stimulation mode. This is done by U3-B, U2-C, U3-F, D9 (LED 17) and R24.

In the search mode the positive terminal of the battery is connected via a resistor 25 (R12) and the secondary of T1 to the (positive) output electrode 4. The body is connected between the (positive) electrode 4 and (negative) electrode 11 as a load. The negative terminal of the battery is connected to electrode 11 through a 2 Mohm resistor 26 (R17). The more conductive the body is, the more current will flow through it and the larger the voltage drop over resistor 26 (R17) will be. The voltage drop is sensed by an integrated circuit IC1 which functions as a voltage controlled oscillator (VCO). IC1 outputs an audio frequency via a driver U3-E to a speaker or buzzer B1. A resistor R20 helps drive B1 which is a capacitive load. The minimum and maximum frequencies of the buzzer B1 are determined by C8, R18 and R19 on IC1. C7 is used to filter out powerline noise. R15 is used to bias the input to the VCO input and maximize the dynamic range. R16 protects the VCO from excess input current. R21 and D5 are used to mute the VCO during the stimulation mode and to modulate it during the search mode. D4 is to prevent negative voltage at the negative output during stimulation.

In the search mode transistors Q3 and Q4 are cut-off and do not play any role. Stimulation control circuit 26 outputs a high signal to NOR gates U2-A, U2-B via inverter U3-B so that a low is always output from the NOR gates, turning the FET's 22a, 22b off.

A low battery indicator 29 utilizes the threshold of U4-D and compares a reference voltage (D7, R22, C6) to the battery voltage. When the battery voltage times the threshold is lower than the reference voltage—the LED 16 (D8) will flash. This circuit utilizes also drivers (U3-C, U3-D) to drive DB. R23 is to limit the current via D8. The power switch 14 is part of the intensity potentiometer.

The stimulation signal is a bipolar 16 $HZ_z$ pulse train. Its intensity is controlled by the user. The peak amplitude is variable between about 40 and 90 volts, giving a maximum instantaneous current up to about 9 mA, whilst the time average DC current is nil. The pulse width is 130 microseconds and the polarity alternates. By stimulating with a 16 $HZ_z$ signal (i.e. 32 pulses per second) the device is using what is felt to be a natural electrical resonance frequency of the body which is optimal for affecting sodium—potassium balance which is important in the operation of the nervous system. It is thought necessary to provide a high voltage (greater than about 40 Volts) to stimulate the system. The voltage is therefore pulsed so that the intensity of the stimulus (the power supplied to the body) over a period of time is quite small, to avoid burning the skin.

The bipolar signal is thought to stimulate in each direction a different nerve path connected to the acupuncture point. In this way more nerve cells are stimulated while the basic resonance frequency is preserved. Since the signal has no overall DC component, little or no electrolytic action should take place and the body's internal chemical balance is not disturbed by it nor the skin irritated by its by-products. Also it is thought that the nerve path will not 'learn' the signal.

The passive electrode 11 provides a large area of contact, with the skin preferably greater than about 1 square centimetre, and hence low current density at the web of the hand; whilst the small area of the active electrode 4 will provide a relatively high current density at the low resistance point, which is the region to be stimulated.

The device is activated by turning the power switch 14 on. The unit is then in the "search" mode. This is indicated by an audio sound at a low pitch from buzzer B1.

The unit is held in the hand (FIG. 3) with electrode 11 making contact with the skin between the thumb and forefinger. To start detection, the tip is moved over the desired area keeping an even pressure on the skin. A chart can be provided to indicate the approximate location of low resistance points. As a low resistance point is reached the pitch increases. Once the point is passed, the pitch will go low again.

Once a desired point is detected, stimulation can be started. The desired stimulation time is selected by setting the time selector (switch 13) accordingly giving a preset time—15 or 30 seconds, or manual stimulation. The "stimulate" button 15 is pressed and stimulation begins. The audio sound stops and LED 17 flashes. The stimulation intensity is adjusted by slide switch 12 to a comfortable level. If a preset stimulation time was selected, pushing the stimulation button again after the time period will automatically stimulate for the selected time again. After the stimulation time is over the unit automatically switches to "search" mode again and the audio sound returns.

Controls may be provided for varying the frequency and pulse width of the stimulation signal, and the sensivity in the search mode. A second jack may be provided for connection of a remote passive electrode in place of the electrode 11; this is of advantage if the device is being used by a therapist. The remote electrode is attached to a low resistance part of the patient's body and electrode 4 is then passed over the patient's body for treatment. It is possible for the device to be used by a therapist with the circuit between electrodes 11 and 4 being completed by both the therapist's and patient's bodies, the therapist touching the patient's skin with his hand.

Various modifications may be made to the described embodiment and it is desired to include all such modifications and mechanical and functional equivalents as fall within the scope of the accompanying claims.

What is claimed is:

1. A hand-held electro-therapeutic device for applying electrical stimuli to selected points of contact on the body of a user, the device comprising
   a casing which is holdable in the hand,
   mounted to the casing a first active electrode for making electrical contact with a selected point of the body and a second passive electrode disposed on the casing for making electrical contact with the hand,
   voltage applying means for applying an alternating voltage across the electrodes to pass an alternating current through the body of the user to apply the stimuli thereto, and
   resistance detecting means for detecting when the first electrode is located at or near a low resistance point on the body, said resistance detecting means comprising means for detecting variations in the resistance between the electrodes and means providing an audible signal representative of the resistance,
   wherein the casing is elongate and the first electrode is mounted at one end thereof, the casing having transverse to an elongate direction thereof, a cross-section having major and minor axes, the major axis being longer than the minor axis, the second electrode being mounted on a wall of the casing on the major axis.

2. A device as claimed in claim 1, in which the means providing an audible signal emits a sound which changes volume or pitch, the volume or pitch being proportional to the resistance.

3. A device as claimed in claim 1, in which the major axis is about three times as long as the minor axis.

4. A device as claimed in claim 1, in which the casing comprises a pair of substantially flat, parallel sidewalls joined at upper and lower edges thereof by upper and lower walls.

5. A device as claimed in claim 4, in which the lower wall is arcuate.

6. A device as claimed in claim 1, in which the casing comprises an upper wall having control means for starting the application of a stimulating voltage across the electrodes.

7. A device as claimed in claim 1, in which the alternating voltage has a bipolar pulsed waveform.

8. A device as claimed in claim 7, in which the waveform has a frequency of about 16 Hz.

9. A device as claimed in claim 1, in which the alternating current of said stimuli has no DC component.

10. A device as claimed in claim 1 in which a battery power supply for said device is housed in the casing.

11. A device as claimed in claim 1 including timing means for controlling the stimuli to be applied for a predetermined time period.

12. A hand held electro-therapeutic device for applying electrical stimuli to selected points of contact on the body of a user, the device having a search mode and a stimulation mode and comprising
    a casing which is holdable in the hand,
    mounted to the casing a first active electrode for making electrical contact with a selected point on the body and a second passive electrode disposed on the casing for making electrical contact with the hand,
    voltage applying means for applying, in said stimulation mode, an alternating voltage across the electrodes to apply electrical stimuli to the body, and
    resistance detecting means for detecting, in said search mode, when said first electrode is located at or near a low resistance point, said resistance detecting means applying a DC voltage across the electrodes and providing an audible signal representative of the resistance,
    wherein in said search mode said electrodes are connected across a DC power supply and in said stimulation mode said first and second electrodes are connected to a common point by means of respective first and second transistors, each transistor having a respective first or second diode connected there-across to allow current to flow between said electrodes in a first direction via the first transistor and second diode and in a second direction via the second transistor and first diode.

13. A hand-held electro-therapeutic device for applying electrical stimuli to selected points of contact on the body of a user, the device comprising
    a casing arranged to be held in the hand,
    mounted to the casing a first active electrode for making contact with selected point of the body and a second passive electrode disposed on the casing for making electrical contact with the hand, and
    resistance detecting means for detecting when the first electrode is located at or near a low resistance point on the body, and
    voltage applying means in the casing for applying a voltage across the electrodes to pass a current therebetween through the body of the user, wherein the voltage applying means comprises means for applying an alternating voltage between the electrodes to apply electrical stimuli to the body of the user, and includes a transformer having a centre-tapped primary winding, a capacitor connected to the centre-tap and an oscillator which alternately grounds either end of the primary winding to discharge the capacitor therethrough, the transformer also having a secondary winding with one end connected to one of the electrodes and another end connected to the other electrode by a pair of back to back transistors each having a diode connected thereacross.

* * * * *